US00PP36898P2

(12) United States Plant Patent
Danziger

(10) Patent No.: US PP36,898 P2
(45) Date of Patent: Aug. 19, 2025

(54) ***IMPATIENS* PLANT NAMED 'DIMPSLPRWT'**

(50) Latin Name: *Impatiens hawkeri*
Varietal Denomination: DIMPSLPRWT

(71) Applicant: Danziger "DAN" Flower Farm, Beit Dagan (IL)

(72) Inventor: Gavriel Danziger, Beit Dagan (IL)

(73) Assignee: Danziger "DAN" Flower Farm (IL)

( * ) Notice: Subject to any disclaimer, the term of this patent is extended or adjusted under 35 U.S.C. 154(b) by 0 days.

(21) Appl. No.: 19/026,204

(22) Filed: Jan. 16, 2025

(51) Int. Cl.
*A01H 6/16* (2018.01)
*A01H 5/02* (2018.01)

(52) U.S. Cl.
USPC ..... Plt./318.2

(58) Field of Classification Search
USPC ..... Plt./318.2
CPC ..... A01H 6/165; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Impatiens* plant named 'DIMPSLPRWT' is disclosed, characterized by large white flowers with pink centers. Plants are sun resistant have mounded habits and dark olive-green foliage. The new variety is an *Impatiens*, typically produced as an ornamental plant.

2 Drawing Sheets

Latin name of the genus and species: *Impatiens hawkeri.*
Variety denomination: 'DIMPSLPRWT'.

BACKGROUND OF THE INVENTION

The new *Impatiens* cultivar is a product of chance discovery. The new variety is the result of a naturally occurring, whole plant mutation of the unpatented, proprietary variety referred to as *Impatiens* 'BM-17-1000'. The new variety was discovered by the inventor in September of 2022 at a nursery in Moshav Mishmar Hashiva, Israel.

Asexual propagation of *Impatiens* 'DIMPSLPRWT' was first performed by leaf cuttings in July of 2020, at the same nursery in Moshav Mishmar Hashiva, Israel. This and subsequent propagation has shown that the unique features of this cultivar are stable and reproduced true to type in multiple successive generations.

SUMMARY OF THE INVENTION

The cultivar 'DIMPSLPRWT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DIMPSLPRWT'. These characteristics in combination distinguish 'DIMPSLPRWT' as a new and distinct *Impatiens* cultivar:

1. Large, white flowers.
2. Well branched plants.
3. Sun-resistant plants.

PARENT COMPARISON

Plants of 'DIMPSLPRWT' are similar in some horticultural characteristics to the parent. The new variety, however, differs in the following:

1. Flower color of the new variety is white, while the flower color of the seed parent is light salmon.
2. Flowers of the new variety are larger than flowers of the seed parent.

COMMERCIAL COMPARISONS

Plants of 'DIMPSLPRWT' are similar in some horticultural characteristics to the variety *Impatiens* 'SAKIMP027', U.S. Plant Pat. No. 24,320. The new variety, however, differs in the following:

1. Flower color of the new variety is white with a pink center, while the flower color of this comparator is pure white.
2. Flowers of the new variety are larger than flowers of this comparator.
3. Plants of the new variety are larger than plants of this comparator.

Plants of 'DIMPSLPRWT' are similar in some horticultural characteristics to the variety *Impatiens* 'SAKIMP036', U.S. Plant Pat. No. 26,886. The new variety, however, differs in the following:

1. Flower color of the new variety is white with a pink center, while the flower color of this comparator is pure white.
2. Flowers of the new variety are larger than flowers of this comparator.
3. Plants of the new variety have smaller, more controlled habits than plants of this comparator.

BRIEF DESCRIPTION OF THE PHOTOGRAPHS

Figure 1:
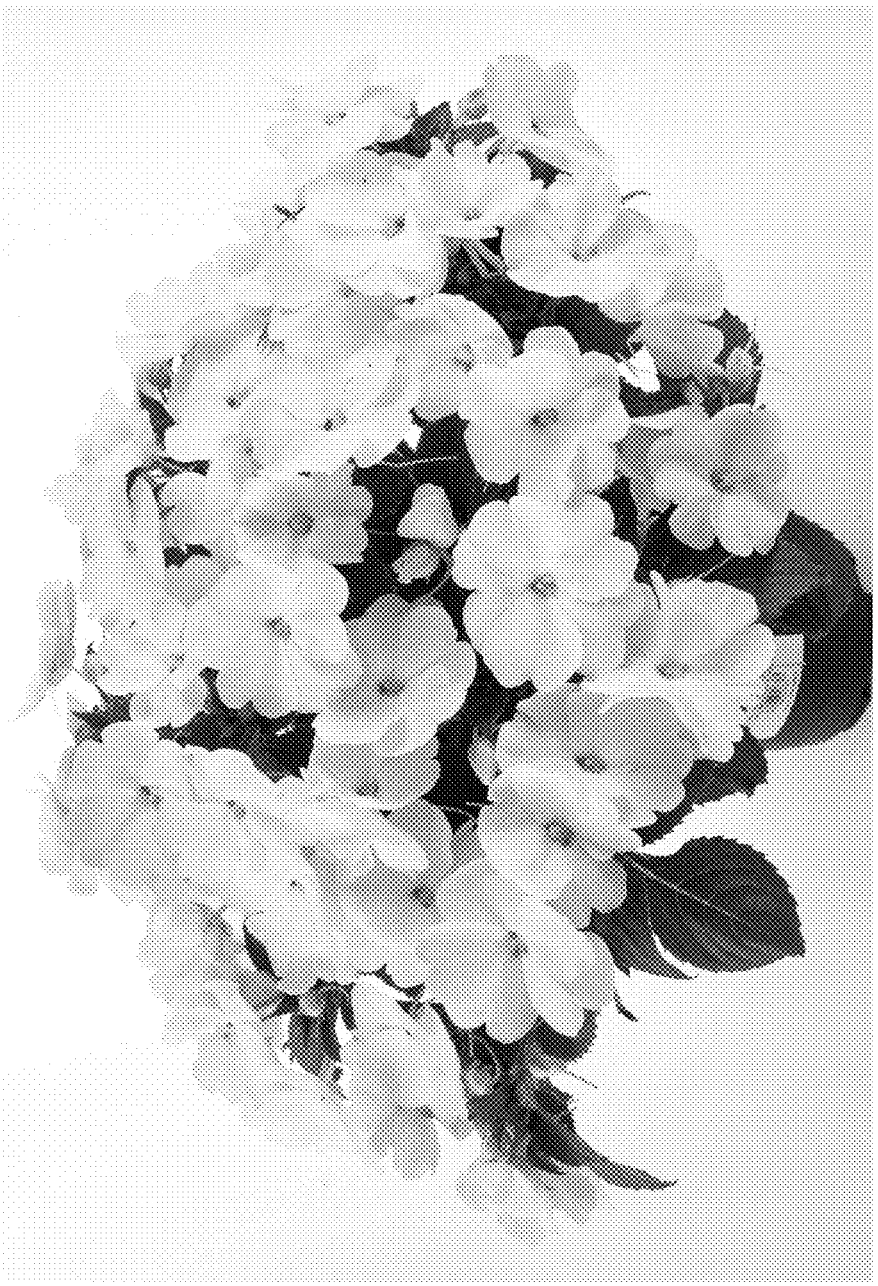

The accompanying photograph in FIG. 1 illustrates in full color a typical plant of 'DIMPSLPRWT' at about 13 weeks of age, grown in a 12 cm pot.

Figure 2:
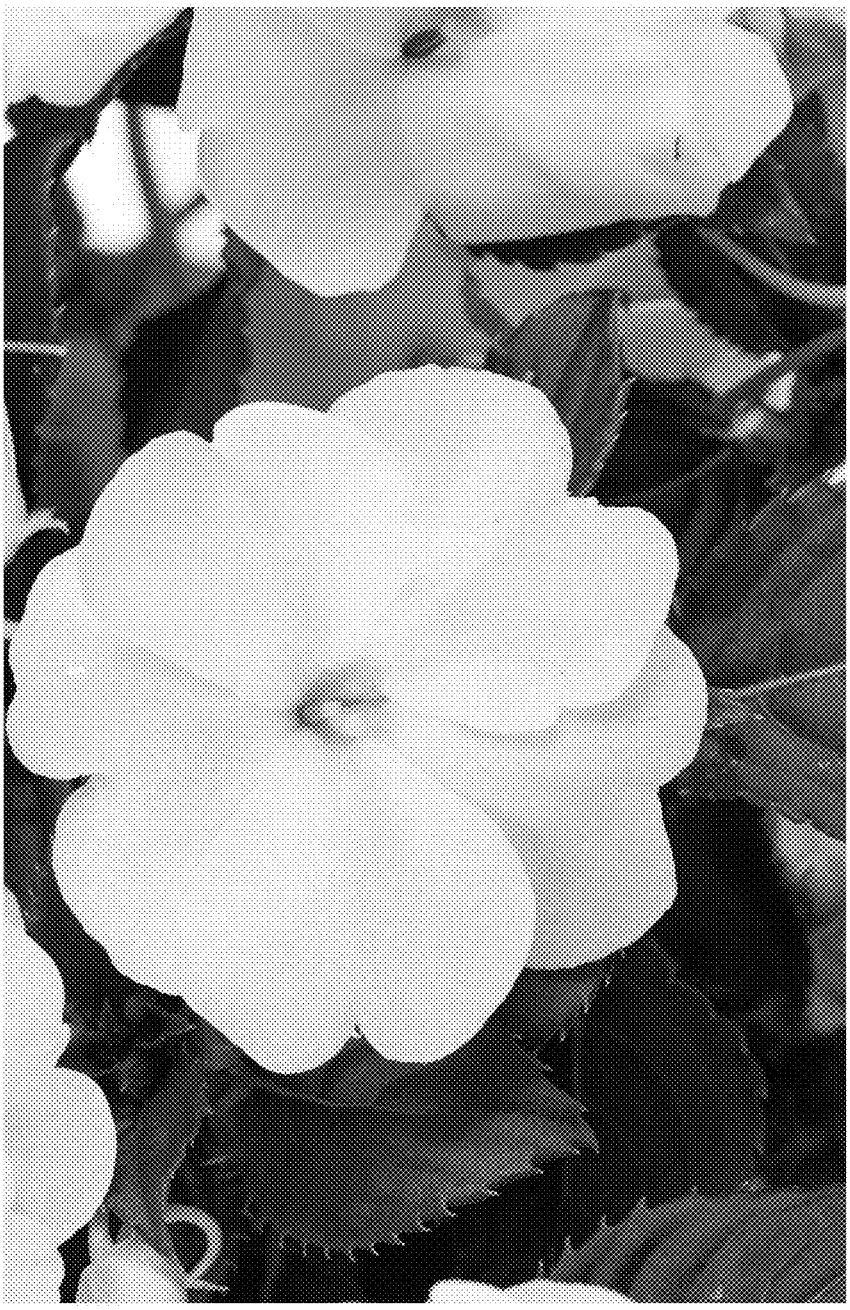

FIG. 2 illustrates a close-up view of a typical flower of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DIMPSLPRWT' plants grown in a greenhouse in Moshav Mishmar Hashiva, Israel, under natural lighting. Measurements were taken during autumn. The growing temperature ranged from approximately 20° C. to 30° C. during the days, 15° C. to 25° C. during the nights. Measurements and numerical values represent averages of typical plant types.

Botanical classification: *Impatiens hawkeri* 'DIMPSLPRWT'.

PROPAGATION

Time to initiate rooting: 10 to 14 days in summer; 14 to 20 days in winter.

Age of plant described: 12 weeks from a rooted cutting.

Root description: Fibrous, adventitious roots.

PLANT

Growth habit: Mounded.

Pot size of plant described: 12 cm.

Height: 20 to 25 cm.

Plant spread: 30 to 35 cm.

Growth rate: Medium.

Branching characteristics: Medium branched.

Length of lateral branches: 15 to 20 cm.

Quantity of lateral branches: 5 to 8.

Characteristics of primary lateral branches:

- *Shape*.—Oval.
- *Diameter*.—1 cm.
- *Texture*.—Smooth.
- *Strength*.—Strong, very stable.
- *Color*.—RHS Yellow-Green 147C.

Internode length: 4 to 5 cm.

FOLIAGE

Leaf:

- *Arrangement*.—Alternate.
- *Quantity*.—Approximately 25 to 30 per branch.
- *Average length*.—7 cm.
- *Average width*.—4 cm.
- *Pubescence*.—None.
- *Shape*.—Lanceolate.
- *Apex*.—Apiculate.
- *Base*.—Acuminate.
- *Margin*.—Ciliate.
- *Texture*.—Smooth.
- *Aspect*.—45°.
- *Color*.—Young Foliage, Upper Side: RHS Yellow-Green 147A. Young Foliage, Under Side: RHS Yellow-Green 147C. Mature Foliage, Upper Side: RHS Green N137B. Mature Foliage, Under Side: RHS Yellow-Green 147C.
- *Venation*.—Type: Pinnate. Color, Upper Side: RHS Yellow-Green 147D. Color, Under Side: RHS Yellow-Green 147C.

Petiole:

- *Length*.—0.5 to 1 cm.
- *Diameter*.—0.2 to 0.3 cm.
- *Color*.—RHS Yellow-Green 145B.
- *Texture*.—Smooth.

FLOWER

Natural flowering season: Flowers at any day length. All year round in a greenhouse environment. Flowering is continuous from spring until fall in an outdoor garden.

Days to flowering from rooted cutting: 10 weeks.

Inflorescence and flower type and habit: Single flowers raised above the foliage. Corolla consists of 5 petals.

Rate of flower opening: 10 to 15 days from bud to fully opened flower.

Flower longevity on plant: 5 to 8 days.

Persistent or self-cleaning: Self-cleaning.

Bud:

- *Shape*.—Ovate.
- *Length*.—1.5 cm.
- *Diameter*.—1 cm.
- *Color*.—RHS White NN155A.

Flower size:

- *Diameter*.—6 cm.
- *Depth*.—6.3 cm including spur.

Petals:

- *Arrangement*.—Overlapping.
- *Length*.—3.5 cm.
- *Width*.—4.5 cm.
- *Quantity*.—5.
- *Texture*.—Smooth.
- *Apex*.—Heart-shaped.
- *Shape*.—Obcordate.
- *Margin*.—Entire.
- *Color*.—When Opening, Upper Surface: RHS White NN155D; spot in center Purple-Pink N66C. When Opening, Lower Surface: RHS White NN155D; spot in center Purple-Pink N66C. Fully Opened, Upper Surface: RHS White NN155D; spot in center Purple-Pink N66C. Fully Opened, Lower Surface: RHS White NN155D; spot in center Purple-Pink N66C.

Spurs:

- *Quantity*.—1 per flower.
- *Length*.—5.5 cm.
- *Diameter*.—0.2 cm.
- *Aspect*.—Spur curvature 40° to 45° from peduncle.
- *Color*.—RHS Purple-Pink 69B towards base; Yellow-Green 149B at apex.

Sepals:

- *Quantity*.—2 per flower.
- *Shape*.—Oblong.
- *Length*.—1 cm.
- *Width*.—0.4 cm.
- *Apex*.—Caudate.
- *Base*.—Rounded.
- *Margin*.—Entire.
- *Color*.—RHS Yellow-Green 145B.

Peduncles:
*Length*.—5 to 5.5 cm.
*Width*.—0.2 cm.
*Angle*.—About 45° to lateral branch.
*Strength*.—Stable, flexible.
*Texture*.—Smooth.
*Color*.—RHS Yellow-Green 145B.
Fragrance: None.

REPRODUCTIVE ORGANS

Androecium:
Stamens:
*Quantity*.—5, with anthers that are more or less fused, forming a cap over the ovary.
Anthers:
*Shape*.—Oblong.
*Length*.—About 0.5 cm.
*Color*.—RHS White 155C.
*Pollen*.—None.

Gynoecium:
Pistil:
*Quantity*.—1.
*Length*.—0.5 cm.
*Style*.—Length: 0.5 cm. Color: RHS Yellow-Green 141B.
*Stigma*.—Shape: Round. Color: RHS Yellow-Green 149D. Ovary Color: RHS Yellow-Green 144D.

OTHER CHARACTERISTICS

Seeds and fruits: 5 to 10 seeds per fruit.
Disease/pest resistance: Neither resistance nor susceptibility of diseases common to *Impatiens* observed.
Temperature tolerance: Tolerant at 30° C. and 5° C. Grows best at 10° C. to 28° C.

What is claimed is:

1. A new and distinct cultivar of *Impatiens* plant named 'DIMPSLPRWT' as herein illustrated and described.

* * * * *